United States Patent [19]

Buschard et al.

[11] Patent Number: 5,827,828

[45] Date of Patent: Oct. 27, 1998

[54] SULFATED GLYCOLIPIDS AND ANTIBODIES THERETO FOR PROPHYLAXIS OR THERAPY OF DIABETES

[75] Inventors: Karsten Buschard, Charlottenlund, Denmark; Pam Fredman, Göteborg, Sweden

[73] Assignee: A+ Science Invest AB, Göteborg, Sweden

[21] Appl. No.: 396,802

[22] Filed: Feb. 28, 1995

Related U.S. Application Data

[63] Continuation of Ser. No. 146,013, filed as PCT/DK92/00146, May 7, 1992, published as WO92/19633, Nov. 12, 1992, abandoned.

[30] Foreign Application Priority Data

May 7, 1991 [DK] Denmark .................................. 0846/91

[51] Int. Cl.$^6$ .......................... A61K 31/70; C07K 16/00; C07H 15/00
[52] U.S. Cl. ................. 514/25; 514/53; 514/54; 514/866; 530/387.2; 530/387.5; 530/388.1; 530/389.1; 536/17.6
[58] Field of Search ............... 530/387.2, 387.5, 530/388.1, 389.1; 514/25, 53, 54, 866; 536/17.6

[56] References Cited

U.S. PATENT DOCUMENTS 5,288,706  2/1994  Yamanouchi et al. ................... 514/15

OTHER PUBLICATIONS

Berkow et al., eds., "The Merck Manual" sixteenth edition, Merck Research Laboratories (Rahway, NJ) 1992, pp. 955–970.

Goodman et al., eds., "Goodman and Gilman's The Pharmaceutical Basis of Therapeutics", Pergamon Press, Inc. (Elmsford, NY) 1990, pp. 1471–1475.

Zubay "Biochemistry", The Benjamin/Cummings Publishing Company, Inc. (Menlo Park, CA) 1983, pp. 20–22.

Stevenson et al., Chem. Abs. No. 78882x, STN International, vol. 116, No. 9 (1992).

Fredman et al. *Biochem. J*. 1988, 251, 17–22.

*Primary Examiner*—Kathleen K. Fonda
*Attorney, Agent, or Firm*—Dinsmore & Shohl LLP

[57] ABSTRACT

Methods for the treatment of prediabetes or diabetes in an individual comprise administering to the individual a therapeutically active agent comprising a glycolipid having a galactose-3-O-sulfate moiety capable of binding to islet cell antibodies. Methods of detecting or quantifying islet cell antibodies in a sample, methods for the detection of Langerhans islet cells, methods for monitoring the development of prediabetes, diabetes or symptoms thereof in an individual and methods for prophylactic treatment against the development of prediabetes or diabetes also involve the use of a glycolipid having a galactose-3-O-sulfate moiety.

30 Claims, 15 Drawing Sheets

SULFATED GLYCOLIPIDS AND ANTIBODIES THERETO FOR PROPHYLAXIS OR THERAPY OF DIABETES

This application is a continuation of application Ser. No. 08/146,013, filed Dec. 13, 1993, now abandoned, which is a continuation of PCT/DK92/00146, filed as PCT/DK92/00146 May 7, 1992 published as WO92/19633 Nov. 12, 1992, the contents of which are incorporated herein by reference.

BACKGROUND OF THE INVENTION

Insulin-dependent (type 1) diabetes is a disease in which both humoral and cellular immunological mechanisms seem to play a role in the pathogenesis. For the study of type 1 diabetes there are several animal models, of which the BB rat is among the most important. The BB rat spontaneously develops diabetes at the age 60–120 days, and the diabetes is dependent on a functional thymus-dependent immune system. Lymphocyte infiltration (insulitis) occurs in the islets of Langerhans, and autoantibodies against islet cells can be detected. Some groups have been able to raise islet-cell-specific monoclonal autoantibodies from the BB rat or the composite NOD mouse.

The recognition of relevant beta cell antigen(s) seems crucial for an understanding of the disease mechanisms behind diabetes mellitus, for a possible prevention of the disease, and for a detection of relevant marker antibodies.

Quantitatively changed antigen expression, dependent on the degree of function, might be a mechanism relevant to several study findings which indicate a diabetogenetic importance of the degree of insulin production. Among the most important studies, the following should be mentioned.

Increased incidence of diabetes is seen after increased insulin-production. In the low-dose streptozotocin diabetic mouse model there is, after ventromedial lesion of the hypothalamic region, a higher incidence and a more severe diabetes. In humans there is an increased incidence of true insulin-dependent diabetes in the last trimester of pregnancy, a period characterized by high insulin output from the beta-cells.

Decreased incidence of diabetes is seen after decreased insulin-production. In the BB rat there is a lower incidence of diabetes, if prophylactic insulin treatment is given during the diabetes-risk period, a procedure which reduces the in situ production of insulin. In the low-dose streptozotocin model there is a lower incidence of diabetes after diet containing low amounts of carbohydrate.

Finally, hyperinsulinsemia is observed in relation to the diabetogenesis. In the EMC-M virus mouse model there are high insulin concentrations in peripheral blood before the onset of clinical diabetes. In parallel, human first-degree relatives of diabetic patients show increased insulin-response to glycaemic stimulus.

Recently, several groups have suggested different proteins as antigen-candidates; these include glutamic acid decarboxylase (64 kD autoantigen), heat-shock protein 65, and a 38 kD protein in the membrane of the insulin secretory granule. However, the antigen could as well be of non-protein structure and, in fact, islet cell antibodies (ICA)—present in the majority of the diabetic patients at diagnosis and labelling both beta and alpha cells—are believed to be directed against a glycolipid. Furthermore, several monoclonal antibodies directed against beta cells have a ganglioside epitope (3G5, A285, R2D6).

Sulfatide (3'-sulfogalactosylceramide) is an acidic glycosphingolipid located at the cell membrane. It is an early marker for the differentiation of oligodendrocytes and Schwann cells (Zalc, B. and Baumann, N., Adv. Exp. Med. Biol. 152: 439–443, 1982) and becomes highly enriched in the myelin.

With the aim to produce an antibody to sulfatide that was specific enough to be used for the quantitative assay of sulfatide in tissues and body fluids in demyelinating disorders, Fredman et al. (Biochem. J. 251: 17–22, 1988) produced the monoclonal antibody Sulph I. Balb/c mice were immunized with sulfatide coated on *Salmonella minnesota* membrane. Spleen cells from the mice were fused with mouse myeloma cells, the resulting hybridomas were screened against sulfatide by an ELISA method, and positive hybrids were cloned by limiting dilution. The subclass of the antibody was found to be IgG1.

Fredman et al. found that the monoclonal antibody Sulph I have affinity to three glycolipids: galactosylceramide-3-sulfate (sulfatide), lactosylceramide-3-sulfate and seminolipid. These three glycolipids all have the same terminal group: galactose-3-O-sulfate. The non-sulfated glycolipids, galactosylceramide and lactosylceramide, and also some bis-sulfated mucopolysaccharides did not bind the antibody. Removal of the fatty acid from sulfatide and seminolipid resulting in their corresponding lyso compounds gave a remarkable diminution in their binding to the antibody.

Sulfated glycolipids are somewhat unusual molecules. Galactosyl sulfatide is relatively abundant in brain tissue, particularly myelin. It is synthesized by oligodendroglial cells and is a differentiation marker for these cells. In vitro, the biosynthesis and cell surface expression of galactosyl sulfatide on oligodendrocytes is regulated, and culture of these cells in the presence of sulfatide-specific monoclonal antibodies significantly affects cell growth and differentiation.

Although islet cells are believed to be of endodermal origin, recent findings have shown sharing of antigen determinants between islets of Langerhans and neural tissue. Glutamic acid decarboxylase is present in both tissues like different kinds of gangliosides. Furthermore, the statistical coincidence of Type 1 (insulin-dependent) diabetes and the neurological disorder "Stiff man syndrome", and possibly also "Guillian-Barré syndrome" (inflammatory demyelinating polyradiculoneuropathy), strengthens the interest in possible joint antigens. In Guillian-Barré syndrome, patients display anti-sulfatide antibodies and by using the monoclonal anti-sulfatide antibody, Sulph I, Fredman et al. (above) have shown structural changes involving the corresponding antigen in the form of demyelinization.

FINDINGS ON WHICH THE INVENTION IS BASED

The following Example 1 examines the presence of sulfatide (or very similar sulfated glycolipids) in islet cells and especially in beta cells; the possible labelling by Sulph I was investigated on pancreatic histological sections as well as on isolated islet cells and on the beta cell fraction and the non-beta cell fraction thereof, separated by means of a fluorescence activated cell sorter.

It was shown that an epitope on the glycolipid sulfatide or on closely related structures are present in islet cells—both beta and non-beta cells—but seems not to be detectable in other examined cells apart from tubular and glomerular cells in the kidney and neural tissue. Furthermore, the used antisulfatide monoclonal antibody gives a very bright staining of islets of Langerhans which may be advantageous for a convenient and reliable detection of islet cells.

Islet cell antibodies (ICA) from Type 1 diabetic patients label—like Sulph I—both beta cells and alpha cells, and increasing evidence indicates that ICA are directed against a glycolipid. On frozen sections, the islet cell antigen has been found to have properties of a sialic-acid-containing glycolipid. ICA reactivity of sera could be blocked by preincubation with monoanglioside-glycolipid extracts from human pancreas. Furthermore, human islets contain $G_{M1}$–$G_{M2}$ ganglioside and, in studies using rat islets, the expression of the gangliosides was metabolically regulable similar to what has been found for the antigens corresponding to the monoclonal antibodies IC2 and A285. Type 1 diabetic sera displayed reactivity against another ganglioside ($G_{T3}$) from RIN tumors. Finally, autoantibodies to human pancreatic fucogangliosides in the sera of ICA-positive Type 1 diabetic patients have been described using thin layer chromatography.

The following Example 2 investigates islets of Langerhans for sulfatide structures, as demonstrated by staining with the monoclonal anti-sulfatide antibody, Sulph I. Since an (auto)immune etiopathogenesis to diabetic late complications has been suggested, also kidney tissue as well as neurological structures were investigated. Furthermore, patients with newly diagnosed Type 1 diabetes were examined for the presence of anti-sulfatide antibodies.

A distinct staining by Sulph I of islets of Langerhans and of tubular structures and glomeruli in the diabetic kidney was found, and in peripheral blood anti-sulfatide antibodies related to Type 1 diabetes were demonstrated.

This investigation showed labelling of islets of Langerhans, kidney structures and neural tissue by the same monoclonal antibody, Sulph I, which is directed against sulfatide. The tissues mentioned all suffer during the natural course of Type 1 diabetes.

By immunoelectronmicroscopy the Sulph I labelling of alpha and beta cells was found to be related to the membrane and the content of the secretory granules. Also ICA seems to label the membranes of insulin-secretory granules. Likewise, the Type 1 diabetic T-cell reactive 38 kD protein involves the insulin-secretory-granule membrane. Carboxypeptidase H, a possible beta cell autoantigen identified as a target of ICA in a lambda GT11 cDNA library, is an enzyme within the beta cell secretory granule and exists as a membrane and (?) soluble form. On the other hand is GAD described to be localized around synaptic-like microvesicles in beta cells.

Staining of the glomeruli with Sulph I was seen both in BB rat and in man, but only when Type 1 diabetes was developed. Labelling of mesangial cells and capillary loops was seen, whereas basal membranes remained unstained. The reason for the diabetic labelling is unknown. It is unlikely that the staining is caused by substantial deposits since diabetes does not induce morphological changes in the BB rat glomeruli, except for thickening of the basement membrane. Thus, no changes in the diabetic BB rat glomeruli are seen in the cells associated with the peripheral capillary wall, in the fractional volumes of the mesangial cells or of the mesangial matrix. Between membranous glomerulopathy and Guillian-Barré syndrome, a link has been suggested, but proof of an association between these diseases does not exist. Furthermore, the Guillian-Barré nephropathy does not necessarily depend on antigen share but might solely be due to immune complexes having their primary origin in the demyelinization process.

Staining of the distal tubuli with Sulph I is in good agreement with earlier demonstration of sulfatide in these structures. It has been suggested that sulfatide in the tubuli is implicated in the passive diffusion of sodium chloride from the lumen into the interstitial space.

In Guillian-Barré syndrome anti-sulfatide antibodies are seen. Since the present study by using Sulph I has demonstrated sulfatide in islet cells (as in neural tissue) we looked for antibodies against sulfatide in newly developed Type 1 diabetic patients and found 88% of them (at the cut off level mentioned in the Result section) to have a titre of up to 1:3200 at diagnosis. Furthermore, in the remission period 6 months later, at which time the disease is stabilizing 59% were positive. Our findings suggest that anti-sulfatide antibodies could be useful as markers for Type 1 diabetes. Today, by far the most commonly used marker is ICA, which is positive in about 70% of newly diagnosed Type 1 diabetics in titres up to 1:128. GAD antibodies have been found to be present in 81% of early stage patients, whereas insulin autoantibodies are detectable in about 40% of newly diagnosed Type 1 diabetics. In monitoring the disease process it seems advantageous to use more than one marker.

Clinical co-incidence between diabetes and neurological disorders is also seen in a diabetes animal model. The strain of encephalomyocarditis virus (EMC-M) used in our laboratory produces diabetes in approximately one third of BALB/c/BOM mice and paresis in about 90 per cent. Attention should be paid to sulfatide as a common antigen but the question of its pathogenetic importance has yet been addressed.

SUMMARY OF THE INVENTION

The foregoing evidence suggests that sulfated glycolipids, in particular such containing galactose-3-O-sulfate, and more particularly galactosylceramide-3-sulfate, lactosylceramide-3-sulfate and seminolipid, are antigens against which Islet Cell Antibodies (ICA) responsible for the development of diabetes and associated complications are raised, and that Sulph I is representative for such ICA.

Accordingly, the invention comprises said sulfated glycolipids and specific catchers therefore (antibodies or lectins) for use in the prophylaxis or thereby of prediabetes, diabetes and/or associated complications in an individual.

By therapy in this context should not be understood the normal substitution therapy (insulin or any substances that stimulate the production of insulin), but any steps taken to stop the destruction or improve the regeneration of beta cells or to prevent the development of complications often associated with diabetes.

The sulfated glycolipids may be used for prophylaxis of prediabetes, diabetes and/or associated complications in an individual by inducing tolerance to such antigens in the individual, for example by perinatal administration of a sulfated glycolipid to said individual. The theory is that by presenting the antigen to the individual at around birth the immune system of the individual will recognize the antigen as belonging to the organism self and will develop tolerance to it.

The sulfated glycolipids may also be used for prophylaxis or therapy of prediabetes, diabetes and/or associated complications in an individual by raising suppressor or regulator cells or antibodies against lymphocytes, recognizing the antigenic sulfated glycolipids, in said individual. This can for example be done by removing lymphocytes from the individual, contacting them with a sulfated glycolipid in vitro to make them recognize this antigen, irradiating the lymphocytes to inhibit their cytotoxicity, and (a) returning them to the individual to raise suppressor or regulator cells or antibodies against lymphocytes reactive with this antigen, or (b) administering them parenterally to another mammal in order to raise antibodies against lymphocytes reactive with this antigen in said mammal and then isolating serum containing the antibodies from said mammal and administering it to the individual.

The sulfated glycolipids may further be used for prophylaxis or therapy of prediabetes, diabetes and/or associated complications in an individual by removing antibodies and/or lymphocytes recognizing the antigenic sulfated glycolipids form the blood stream of the individual. This can for example be done by contacting the blood stream of the individual with an immobilized sulfated glycolipid to remove antibodies and/or lymphocytes recognizing the antigenic sulfated glycolipids from the individual.

The catchers for said glycolipids, and in particular the antibodies directed against them, may also be used for prophylaxis or therapy of prediabetes, diabetes and/or associated complications in an individual by raising anti-antibodies in said individual. This can for example be done by parenterally administering an antibody against sulfated glycolipids, (a) to said individual in a sufficient amount to raise anti-antibodies in said individual, or (b) to another mammal in order to raise anti-antibodies in said mammal and then isolating serum containing the anti-antibodies from said mammal and administering it to the individual.

The invention further comprises the use of sulfated glycolipids in particular such containing a galactose-3-O-sulfate moiety as the antigen in antigen-antibody assays for the detection and, optionally, quantitation of islet cell antibodies (ICA) or other antibodies relevant to prediabetes, diabetes and associated complications in an individual. The antigen-antibody assay is carried out on a sample of body fluid taken from the individual, and as examples of antigen-antibody assays in common use may be mentioned ELISA, radioimmunoassay, countercurrent electrophoresis and immunofluorescence.

The detection and quantitation of ICA or other antibodies relevant to prediabetes, diabetes and associated complications in an individual may serve to assess the risk of said individual for developing diabetes, and repeated quantitations of ICA or other relevant antibodies in the individual may be used to monitor the development of such risk. Likewise, repeated quantitations of ICA or other relevant antibodies in an individual already suffering from prediabetes or diabetes and, possibly, associated complications may be used to monitor the development of the disease and/or associated complications or to monitor the results of a treatment of the disease and/or associated complications.

Finally the invention comprises the use of catchers for sulfated glycolipids, in particular such containing a galactose-3-O-sulfate moiety, for the detection of Langerhans islet cells by histologic or cytologic staining of pancreatic preparations.

I have found that this is a very convenient and reliable method of detecting Langerhans islets in pancreatic tissue preparations as well as isolated islet cells in pancreatic cell fractions. Practical embodiments of histologic staining of pancreatic tissue sections and cytologic staining of isolated cell fractions are illustrated in the following Example 1.

BRIEF DESCRIPTION OF THE DRAWINGS

The figures are reproductions of photographs showing:

FIG. 5. Sulph I-stained pancreatic sections. Original magnification ×66.

FIG. 7. Sulph I-stained kidney sections.

EXAMPLE 1

Materials and Methods

Figure 1:
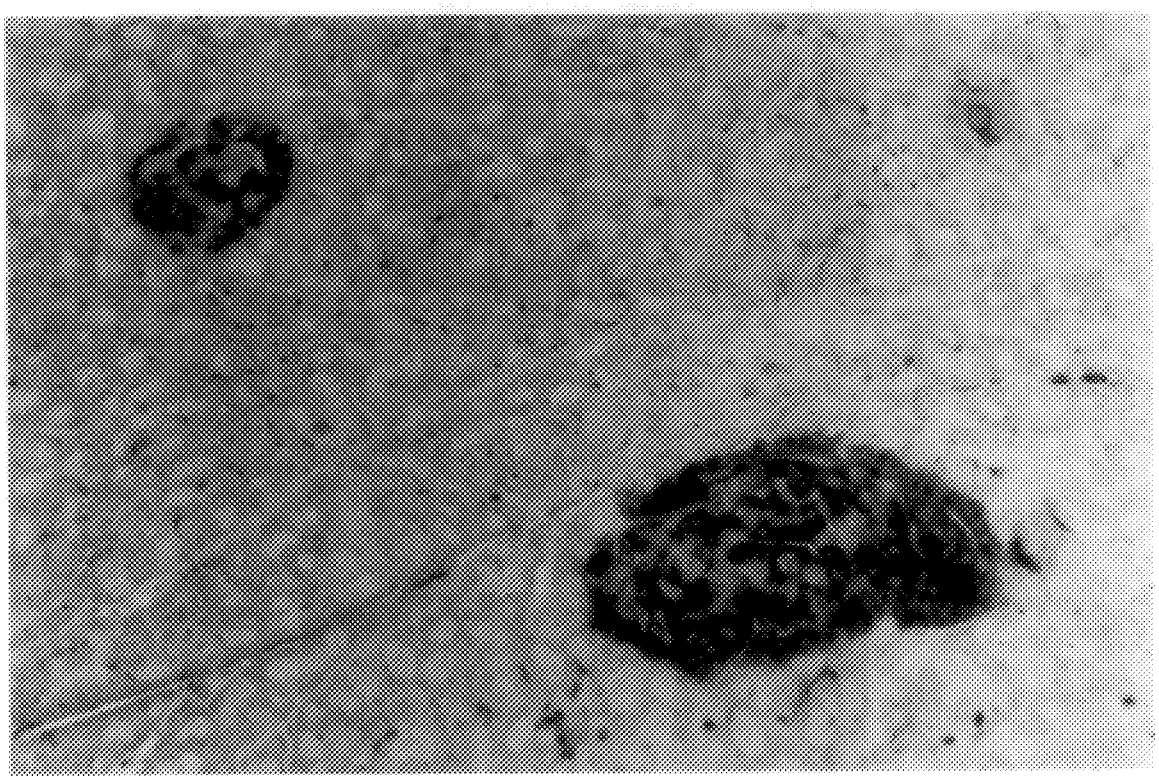
FIG. 1. Labelling by anti-sulfatide monoclonal antibody, Sulph I, of islets of Langerhans in pancreas from a Lewis rat using APAAP technique as described in Example 1, Materials and Methods.

Sulph I antibody.

Sulph I antibody was previously produced by immunizing BALB/c mice with sulfatide coated on *Salmonella minnesota* bacterial membrane (Fredman et al., supra). A subsequent fusion with mouse myeloma cells resulted in a hybridoma producing antisulfatide antibody. The antibody subclass is IgG1.

Tissue origin.

The pancreas tissue examined originated from non-diabetic adults of the otherwise spontaneously diabetic BB rats (Møllegaard, Ll. Skensved, Denmark) and NOD mice (Bartholin Institute colony originating from E. Leiter, Bar Harbor Me.); also Lewis rats (Møllegaard), and BALB/c mice (Bomholtgaard, Ry, Denmark) were studied.

Immunofluorescence microscopy studies.

Frozen tissue sections (5 μm thick) were fixed in acetone at 20° C. for 5 min and after wash incubated with Sulph I, diluted 1:100 for 60 min. As conjugate was used FITC-labelled rabbit-anti-mouse immunoglobulin (F261, Dako, Glostrup, Denmark), diluted 1:30 and incubated for 30 min. The slides were coversliped with PBS glycerol buffer containing p-phenylenediamine (Johnson, G. D. and Araujo, G. M. C. N., J. Immunol. Methods 43: 349, 1981) and were examined for immunofluorescence by a Polyvar, Reichert-Jung microscope.

Alkaline phosphatase anti-alkaline phosphatase (APAAP) method.

Paraffin sections were pretreated with 0.1% protease ()P-8038, Sigma, St. Louis, Mo.) in 0.05M Tris buffer (pH 7.6) for 10 min at room temperature, rinsed in running tap water and 0.05M Tris buffer, pH 7.4 (TBS) for 5 min and incubated with undiluted rabbit serum (Dako) for 5 min. After wash the sections were incubated for 60 min with Sulph I, diluted 1:50 in TBS. As second layer was used rabbit-anti-mouse immunoglobulin (Z259, Dako) diluted 1:50 in TBS and incubated for 30 min. After rinsing in TBS for 5 min the sections were incubated with APAAP-komplex (APAAP, Dako) diluted 1:100 in TBS for 30 min. Following a short rinse in TBS, incubation with enzyme substrate (2 mg Napthol-AS-MX disodium phosphate (Sigma), 2.4 mg Levamisol, and 10 mg Fast Red TR Salt (F-1500, Sigma) in 10 ml 0.1M TBS, pH 8.2) was carried out at 20° C. for 30 min. The sections were counterstained in Mayer's haematoxylin for 1 min and after 5 min in running tap water coverslips were mounted with Aquamount (BDH, Poole, UK).

Isolation of islet cells.

Islets of Langerhans from male Lewis Rats of approximately 10 weeks of age were isolated under sterile conditions by a collagenase digestion technique. In brief, a collagenase (Sigma) and DNase (Worthington, Freehold, N.J.) mixture was injected into the pancreatic duct immediately after the animal had been killed. The pancreas was removed and shaken vigorously (200 strokes/min, 5 cm stroke length) 6 min×2 in a water bath at 37° C. After washing and aspiration, the tissue was centrifuged on "Ficoll" gradient (Pharmacia, Uppsala, Sweden; 13.0, 19.5, 21.5, and 24.0% wt/vol) for 10 min at 800 G. The islets were found in the interphase between 19.5% and 21.5%, and after washing three times the remaining exocrine tissue was removed with a pipette under a stereo microscope. Islets were resuspended in RPMI-1640 with 20 mM HEPES buffer, 10% fetal calf serum, 2 mM 1-glutamine, 4 mM $NaHCO_3$, 0.5% Penicillin-Streptomycin, (10000 IU/ml/ 10000 μg/ml, Gibco, Praisley, UK), adjusted to pH 7.35 and incubated over night at 4° C. The following day the islets were incubated with Dispase (Boehringer Mannheim, Mannheim, Germany) for 5 min×3 at 37° C. and after repeated aspirations the islet cells were separated.

Islet cell sorting using Fluorescence Activated Cell Sorter (FACS).

The islet cell sorting was performed on FACStar Plus (Becton Dickinson, Mountain View, Calif.) operating with a 70 m nozzletip. Autofluorescence was elicited using 488 nm stimulation and 515–545 nm detection. Two populations are readily visible (Van de Winkel & Pipeleers 1983), one low-fluorescence, low-scatter fraction containing 97.8%±1.5% (N=5) endocrine, non-beta cells and one high-scatter, high-fluorescence containing 96.7%±2.6% (N=5) beta cells; the quality of the sortings was checked by electron microscopy, the contaminating cell types were exocrine cells, stroma cells or lymphocytes. Hormone measurements in the supernatant after incubation of islet cell subsets sorted in this way using our FACS, showed for the non-beta cell fraction that 52.9% of the produced hormone was glucagon (27.6% pancreatic polypeptide, 12.5% somatostatin, and 6.9% insulin), further indicating that the majority of the endocrine cells in this fraction were alpha cells. During the sorting, typically $2 \times 10^5$ cells were obtained from the non-beta cell population and $6 \times 10^5$ cells from the beta cell population. The sorted cells were morphologically well preserved.

Antibody labelling.

Before labelling the cells were incubated at 37° C. for 90 min in RPMI-1640 medium as described above. Then 100 μl of medium containing $10^5$ cells was stained with Sulph I diluted 1:100 for 30 min at 0° C. Again, FITC-labelled rabbit-anti-mouse immunoglobulin (F261, Dako) diluted 1:40 and incubated for 30 min at 0° C. was used as conjugate.

Analysis of antibody labelled cells.

For FACS analysis, 2000 cells of each population and each labelling were examined. The background fluorescence profile determined after incubation with an irrelevant anti-CD8 monoclonal antibody (Dako-T8, Dako) and the second layer-antibody, was subtracted from the fluorescence profile detected with the correspondingly Sulph I-labelled samples. The results were expressed as the percentage of positive cells in the total number of cells counted.

For microscopy examination, cells were fixed in 1% formaldehyde. Slides of single cells were prepared with deposits of a droplet containing 100 cells and then dried by airflow, washed with distilled water, and dried again. "Entellan" (Merck, Darmstedt, Germany) was used as mounting medium. With the cover slip the slides could be preserved at 4° C. for several days; as result of the dry environment, there was only minimal fading.

Results

Histologic examination of pancreatic tissue.

A pronounced labelling by Sulph I of the islet of Langerhans was found both using the immunofluorescence and the APAAP technique (FIG. 1). The staining of tissue from the various rat and mouse strains showed similar results; no qualitative difference between BB or Lewis rats, NOD or BALB/c mice were seen but the tissue from the mice tended to be slightly weaker stained. The majority of the islet cells showed staining of their cytoplasma and many of them had in addition nuclear staining; these cells were situated mainly in the periphery of the islets. Several mini-islets were stained as well as duct cells but no labelling of the exocrine cells was detected. By the immunofluorescence method staining of islet cells was seen using Sulph I in dilutions up to 1:1500 and technically good preparations could easily be obtained. This was more difficult when using the APAAP method since long exposure to formelin fixation abolished the antigenicity for Sulph I, and different enzymatic pretreatment could not in all cases unmask the antigen determinants.

Histologic examination of other tissue.

Microscopy of other kinds of tissue showed no labelling by Sulph I in thymus, spleen, lymphnodes, heart, liver, and adrenals. In the kidney, staining of the cytoplasm of some tubular cells and of the mesangium of the glomeruli was seen. In the brain myelin was—s expected—clearly stained.

Cytologic examination of islet cells.

Figure 2:
FIG. 2. Labelling of the beta-cell fraction of isolated islet cells from a Lewis rat with Sulph I and FITC conjugate using immunofluoresence technique as described in Example 1, Materials and Methods. A spackled, bright surface fluorescence of the cells is seen.

By immunofluorescence microscopy examination of both the beta cell fraction and the non-beta cell fraction nearly all the cells showed a bright surface fluorescence after labeling with Sulph I and FITC conjugate. Only very few lymphocyte-resembling cells were negative. As seen from FIG. 2 (beta cell subset) and FIG. 3 (non-beta cell subset) the staining was scattered throughout the cell surface; the intensity of fluorescence seemed to be equal for beta and non-beta cells.

By examination in the FACS 97.3±2.2 (SD)% of the cells in the beta cell fraction and 84.4±3.0 (SD)% in the non-beat cell fraction were Sulph I labelled. The mean channel of fluorescence was similar for the fractions indicating equal intensity of fluorescence.

EXAMPLE 2

Materials and Methods

Patients

The patients consists of 34 newly diagnosed Type 1 diabetics at an average age of 30.1±7.4 (19–54) years [±SD (range)]. Clinical diagnosis of Type 1 diabetes rested on the following criteria: random blood glucose concentration >12 mM, significant ketonuria and glucosuria. Insulin treatment was started on the day of diagnosis and all patients have since continued with this treatment. The patients were examined for anti-sulfatide antibodies 4.0±3.2 (0–12) days after diagnosis and for 18 of them, a second examination was performed on average 187.1±19.5 (156–229) days after diagnosis.

Controls

The controls included of 135 sera or plasma from blood donors (Sahlgrens' Hospital, Göteborg, Sweden, and Bartholin Institutet), 20–60 years of age with equal sex distribution. The sera or plasma were frozen within 24 hours from being drawn and kept at −20° C. until analyzed. None of the samples had been frozen for more than 2 months.

Tissue origin

The pancreatic tissue was obtained from 10 Lewis rats. The rat kidney tissue derived from 10 diabetic and 10 non-diabetic adult BB rats. The rats were purchased from Møllegaard, Lille Skensved, Denmark.

The pig tissue originated from a female Danish.

The monkey tissue was from a male *Macaca facicularis* monkey, 2 to 5 years old from Java, sacrificed for a muscle physiological study and only incidentally used for this study. The tissue was removed immediately after extinction.

The human kidney specimens originated from kidney biopsies taken on account of clinical indications independently of this study. A non-diabetic biopsy was from a 39-year-old female with slight arterial hypertension (180/100 mm Hg). A biopsy from a 62-year-old female with Type 2 diabetes (NIDDM) was taken due to the indication proteinuria, whereas a biopsy from a 23-year-old Type 1 diabetic (IDDM) female patient was performed because of diabetic nephropathy. The kidney biopsies were obtained as earlier described.

Sulph I antibody

The antibody used, Sulph I, was previously produced by immunizing BALB/c mice with sulfatide coated on *Salmonella minnesota* bacterial membrane. A subsequent fusion with mouse myeloma cells resulted in a hybridoma producing anti-sulfatide antibody. The antibody subclass is IgG1. It reacts with sulfatide (3'-sulfogalactosylceramide) and the closely related structures sulfolactosylceramide and seminolipid.

Histological procedures

The alkaline phosphatase anti-alkaline phosphatase (APAAP) method was used. Frozen tissue sections (5 μm thick) were fixed in acetone at 20° C. for 5 min, and after washing incubated for 60 min with Sulph I, diluted 1:100 in Tris buffered saline (TBS). As second layer rabbit anti-mouse immunoglobulin (Z259, Dako, Glostrup, Denmark) diluted 1:50 in TBS and incubated for 30 min was used. After rinsing in TBS for 5 min the sections were incubated with APAAP complex (APAAP, Dako) diluted 1:100 in TBS for 30 min. Following a short rinse in TBS, incubation with enzyme substrate (2 mg naphthol-AS-MX disodium phosphate (Sigma, St. Louis, Mo., USA), 2.4 mg levamisol, and 10 mg fast red TR salt (F-1500, Sigma) in 10 ml 0.1M TBS, pH 8.2) was carried out at 20° C. for 30 min. The sections were counterstained in Meyer's haematoxylin for one min and after five min in running tap water coverslips were mounted with Aquamount (BDH, Poole, UK).

Electron microscopy

Samples (<1 mm$^3$) of rat-pancreative tissue were fixed for 1½ h in a mixture of 3% paraformaldehyde and 0.2% glutaraldehyde. After washings in cacodylate buffer pH 7.3 and dehydration in 70% alcohol specimens were imbedded in LR-white (Bio-Rad, Watford, UK). Ultrasections were incubated with sulph I, diluted 1:1000, for 40 min. Following incubation with rabbit anti-mouse immunoglobulin (F261, Dako) sections were treated with swine anti-rabbit immunoglobulin conjugated with colloidal-gold (10 nm) (G386, Dako). Specimens were after washings postfixed in 2% glutaraldehyde for 5 min and then examined in a JEOL 100-C electron microscope. Controls were treated similarly except for the incubation of the primary antibody.

Serological examinations

Detection of anti-glycolipid antibodies in serum was performed with a thin-layer chromatography (TLC) overlay technique, recently described. The glycolipid antigens[1] used in the assay were: acidic glycolipid extracts from 1 mg wet weight of human brain, including gangliosides GTM1, GTD1a, GD1b, GT1b, and from 10 mg wt weight of human cauda equina, including LK1 and HexLK1 (also designated SGPG and SGLPG, respectively). The other antigens used were pure sulfatide, GA1, 3'-LM1 and galactosylceramide, and 500 pmol of each was applied on the plate. The glycolipid antigens were applied as 5 mm lanes on a TLC-plate (Marchery-Nagel, Düren, Germany) and chloroform/methanol/0.25% KCl (50:40:10 v/v) was used as chromatographic solvent. The plate was then dipped in polyisobutylmethacrylate and preincubated in TRIS-buffer (0.05M TRIS-HCL, pH 7.4, 0.14M NaCl) containing 3% (w/v) dry milk as blocking agent. The plate was then incubated with serum, diluted 1 to 100 or more in TRIS-buffer containing 3% dry milk, and subsequently with alkaline phosphatase-conjugated anti-human IgG or IgM antibodies. Bound antibodies were visualized by incubating the plate with 5-bromo-4-chloro-3-indolylphosphate (Sigma). The tire was determined as the highest serum dilution that gave a positive staining of glycolipid antigen/s (FIG. 1). Among the controls 10 were found to give a detectable reaction with most of the antigens applied. Reactivity against ganglioside LM1 was noticed in 6% of the controls and against LK1 in 1% of the sera. For sulfatide see Result section.

[1]The ganglioside nomenclature used: GM1, II$^3$NeuAc-GgOse$_4$Cer; GD1a, IV$^3$NeuAc, II$^3$NeuAc-GgOse$_4$Cer; Gd1b, II$^3$(NeuAc)$_2$-GgOse$_4$Cer; GT1b, IV$^3$NeuAc, II$^3$NeuAc, II$^3$NeAc-GgOse$_4$Cer; LK1, SO$^3$-3G1cAβ1-3Ga1β1-4G1cNAcβ1-3Ga1β1-4G1cβ1-1Cer; HexLK1, SO$_3$-3G1cA⊕1-3Ga1⊕1-4G1cNAc⊕1-3Ga1β1-4G1cNAcβ1-3Ga1β1-4G1cβ1-1Cer; GA1, GgOse$_4$Cer; 3'-LM1, IV$^3$NeuAc-nLcOse$_4$Cer.

Statistics

The significance of differences was evaluated by the Wilcoxon test. The Spearman's rank correlation test was used for the calculation of the coefficient of correlation.

Results

Investigation of pancreatic tissue

In all the animals examined Sulph I did not react with the exocrine part of pancreas, but solely with the islets of Langerhans; these were, however, very intensely stained (FIG. 2a). The staining of the islets was homogeneous, indicating that both alpha and beta cells were labelled. As can be seen from the figure, several single cell islets and other small islets were visualized.

In pig (FIG. 2b) and monkey (FIG. 2c) pancreatic tissue the same labelling pattern was seen although the staining was weaker.

Electron microscopy

Figure 3:
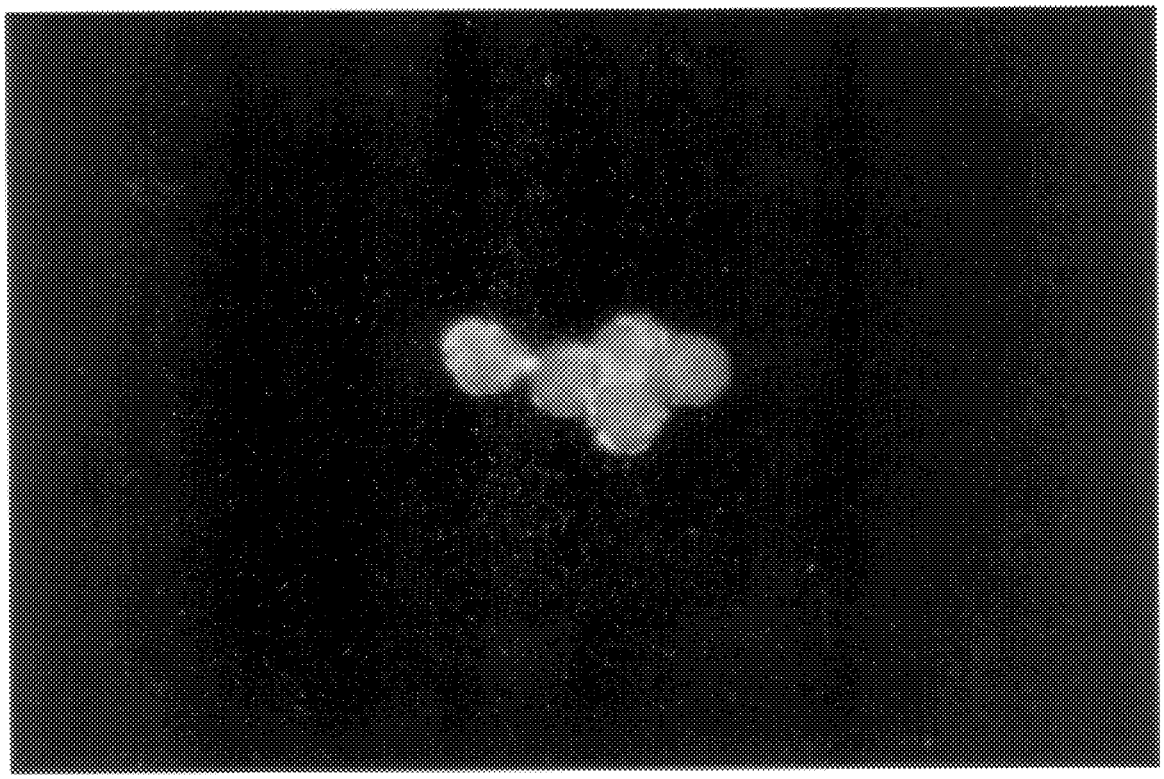
FIG. 3. The same labelling as in FIG. 2 but of the non-beta-cell fraction of islet cells. The intensity of fluorescence after Sulph I staining seems to be equal for beta and non-beta cells.

Immunogold staining showed gold-particles to be concentrated in secretory-granules of both alpha and beta cells (FIG. 3). Furthermore, few particles were located on the outer surface of the cytoplasmic membrane. The presence of few haphazardly distributed particles in the cytosol, occasionally located in mitochondria, were interpreted as nonspecific binding. The control sections were negative.

Investigation of kidney tissue

Figure 4A:
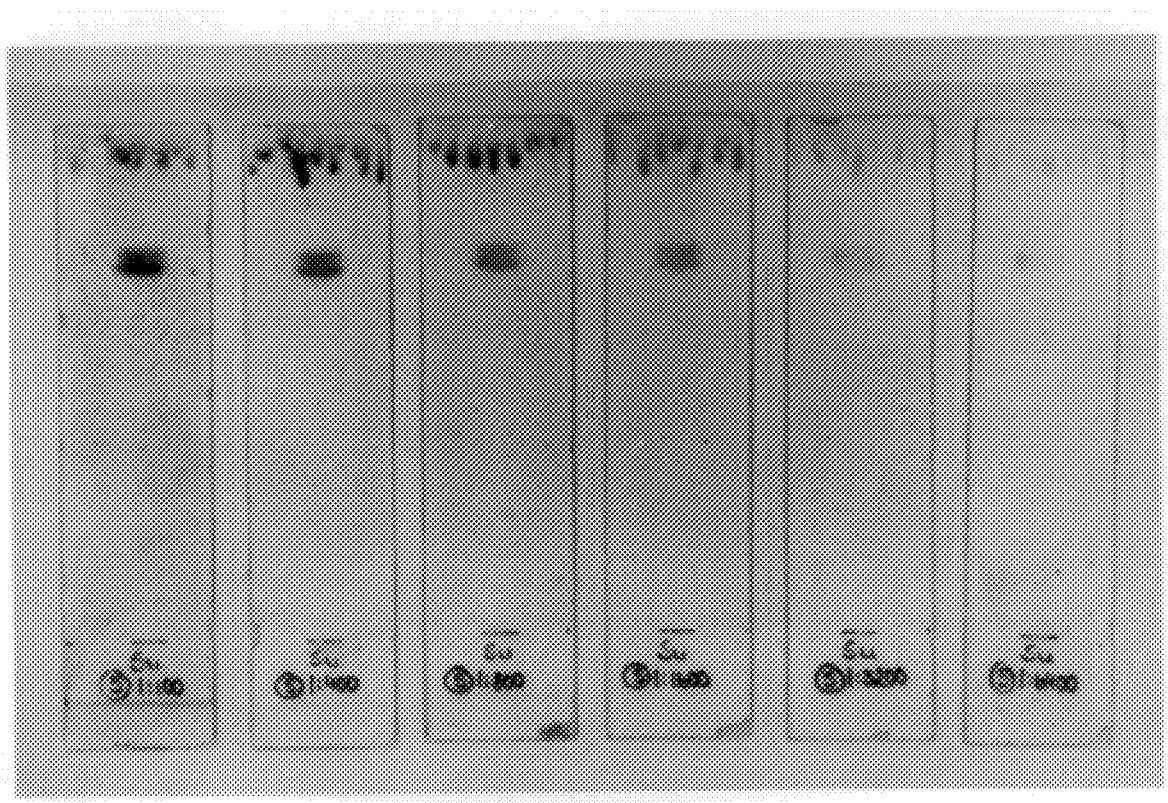
FIG. 4. Sulfatide, chromatographed on thin-layer plate, immunostained with plasma from a newly diagnosed Type 1 diabetic patient. The plasma dilutions are 1:100, 1:400, 1:800, 1:1600, 1:3200 and 1:6400, respectively. The amount of sulfatide applied on the plate was 500 pmol. A detailed description of the chromatography and the immunostaining is given in materials and methods.

FIG. 4 shows kidney sections of different origins stained with Sulph I.

In the monkey kidney (FIG. 4a) the glomeruli are seen without deposits of Sulph I. Around the final corpusculum, a number of tubular profiles are typically seen with heavy granular staining of Sulph I in the tubular epithelium cells. The tubular basement membrane is seen as a distinct uncolored structure. The picture seen in pigs was completely in agreement with that demonstrated in the monkey kidney.

In clinically healthy (non-diabetic) BB rat kidneys (FIG. 4b), a questionable staining was seen in the endocapillary space (plasma proteins?) and in the mesangium of many of the glomeruli. A very heavy staining of the wall of the juxtaglomerular arterioles and of the macula densa area was seen. Also other parts of the tubular system, most probably representing distal tubules, were usually labelled by Sulph I.

Figure 4B:
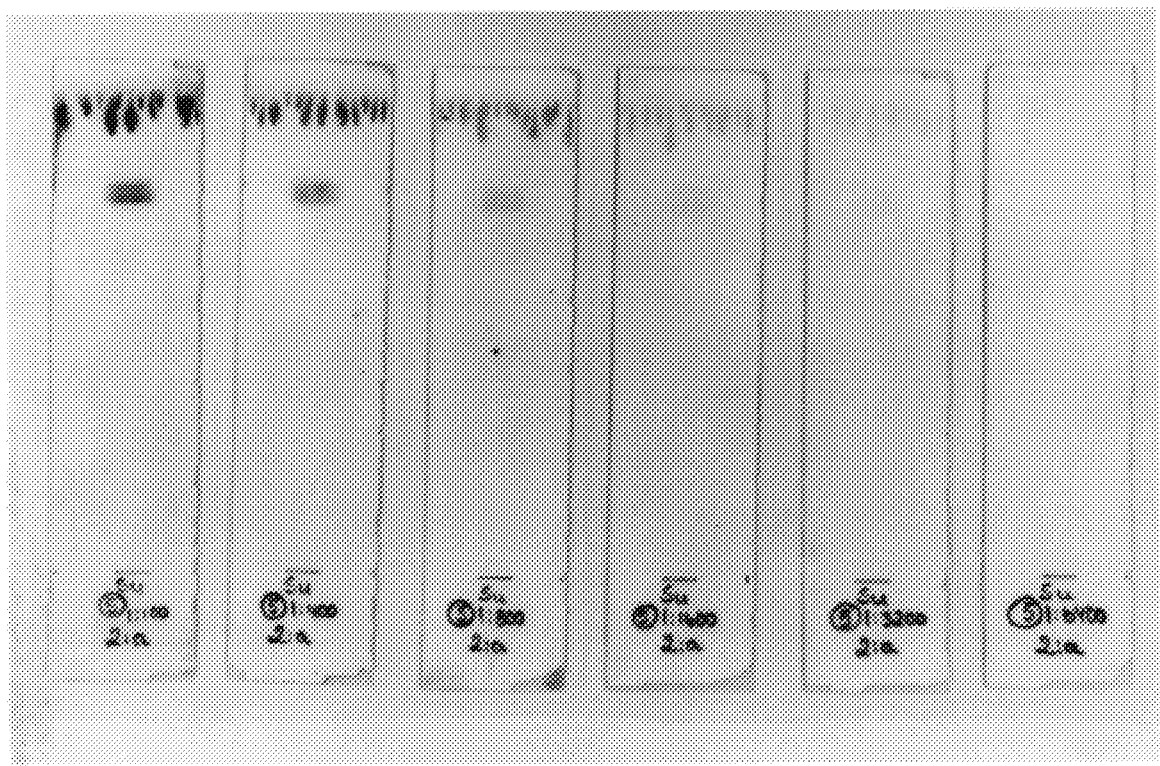
Figure 5A:
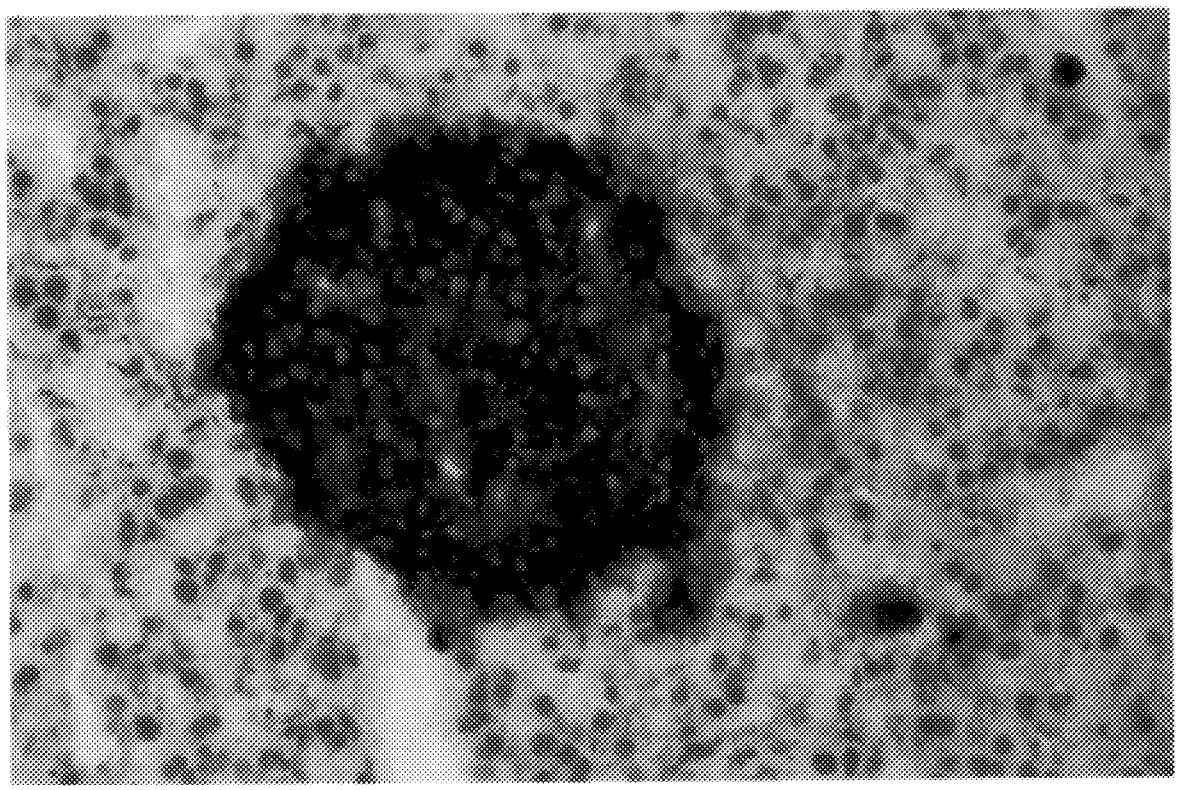
FIG. 5a is from a Lewis rat.
Figure 5B:
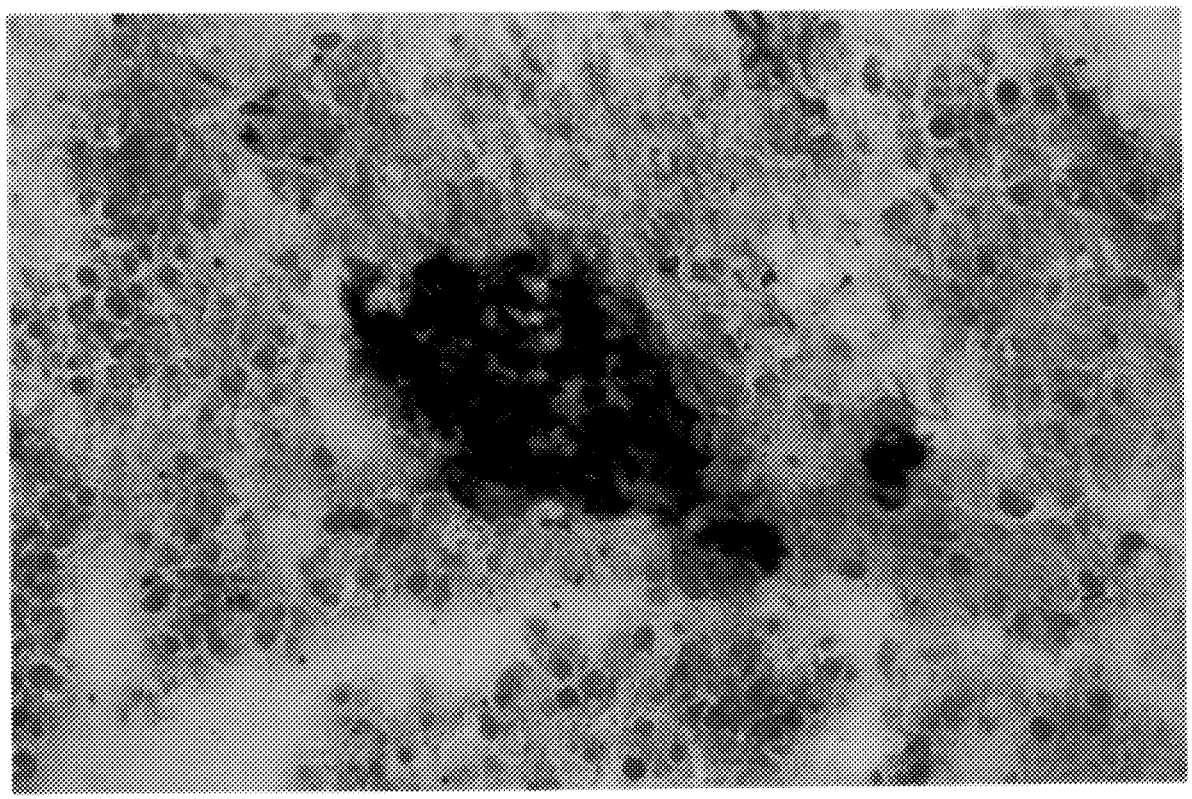
FIG. 5b from a pig.
Figure 5C:
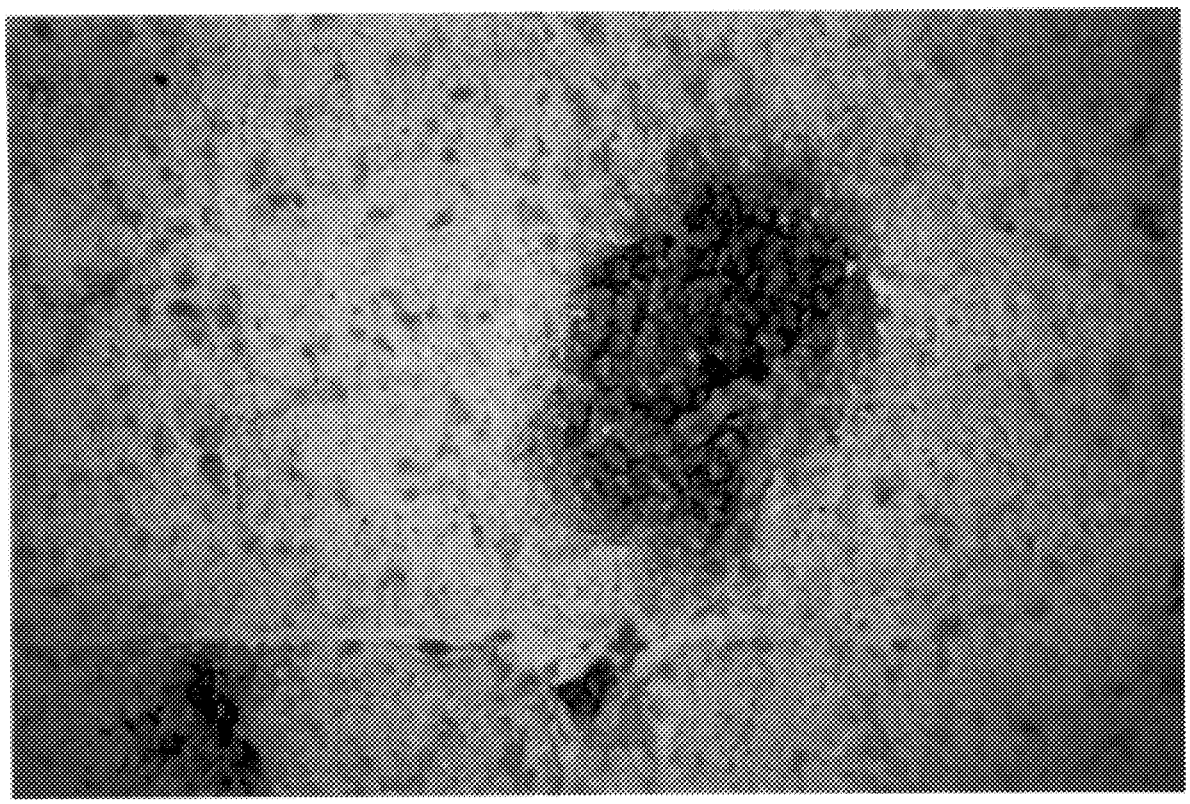
FIG. 5c from a *Macaca facicularis* monkey.
Figure 6:
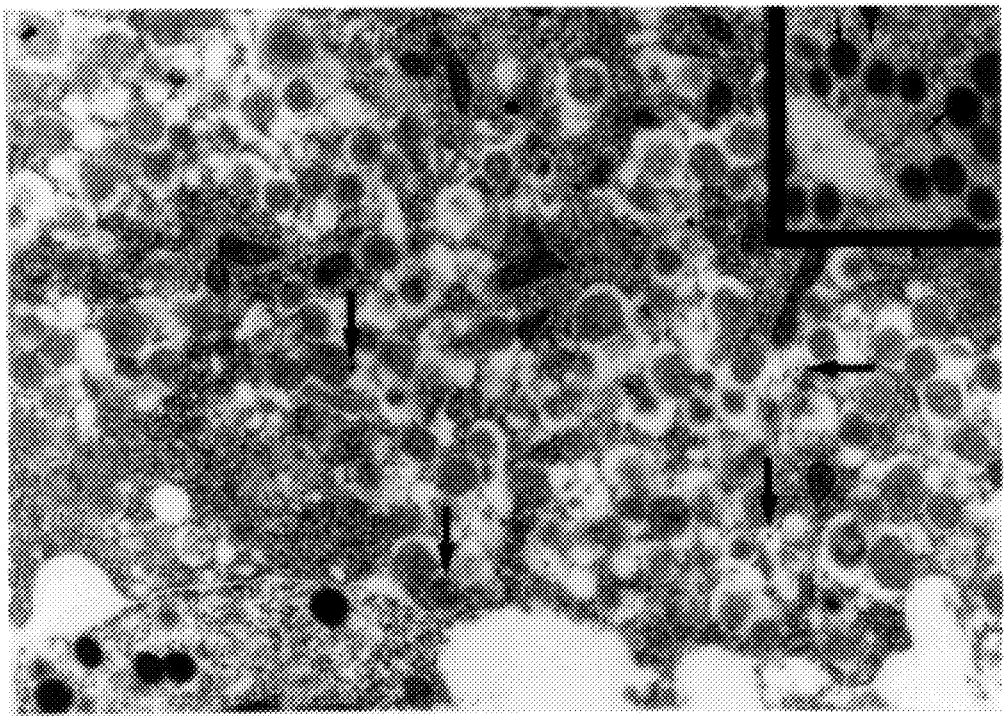
FIG. 6. Electronimicrograph illustrating β-granules (arrows) labelled with 15 nm colloidal-gold. Original magnification ×25.000.
Figure 7A:
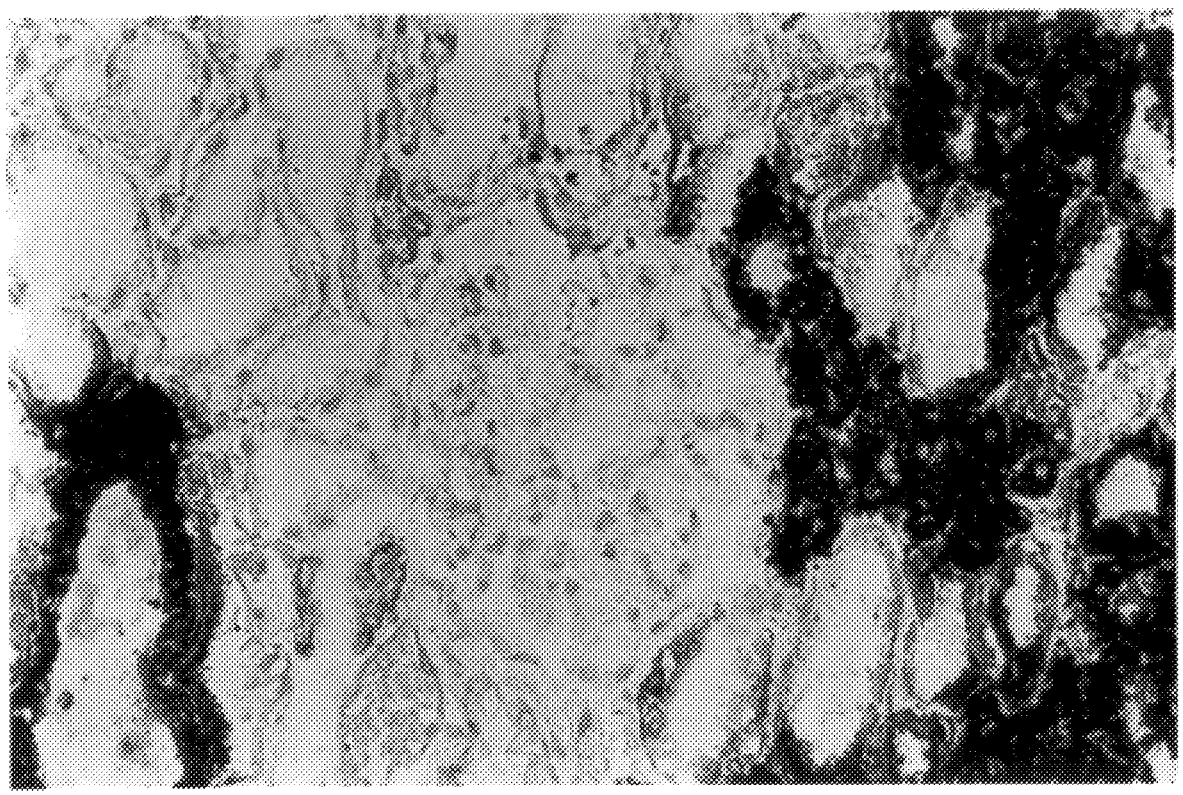
FIG. 7a is from a *Macaca facicularis* monkey (original magnification ×80); arrows indicate the tubular basement membrane which is seen as a distinct uncolored structure.
Figure 7B:
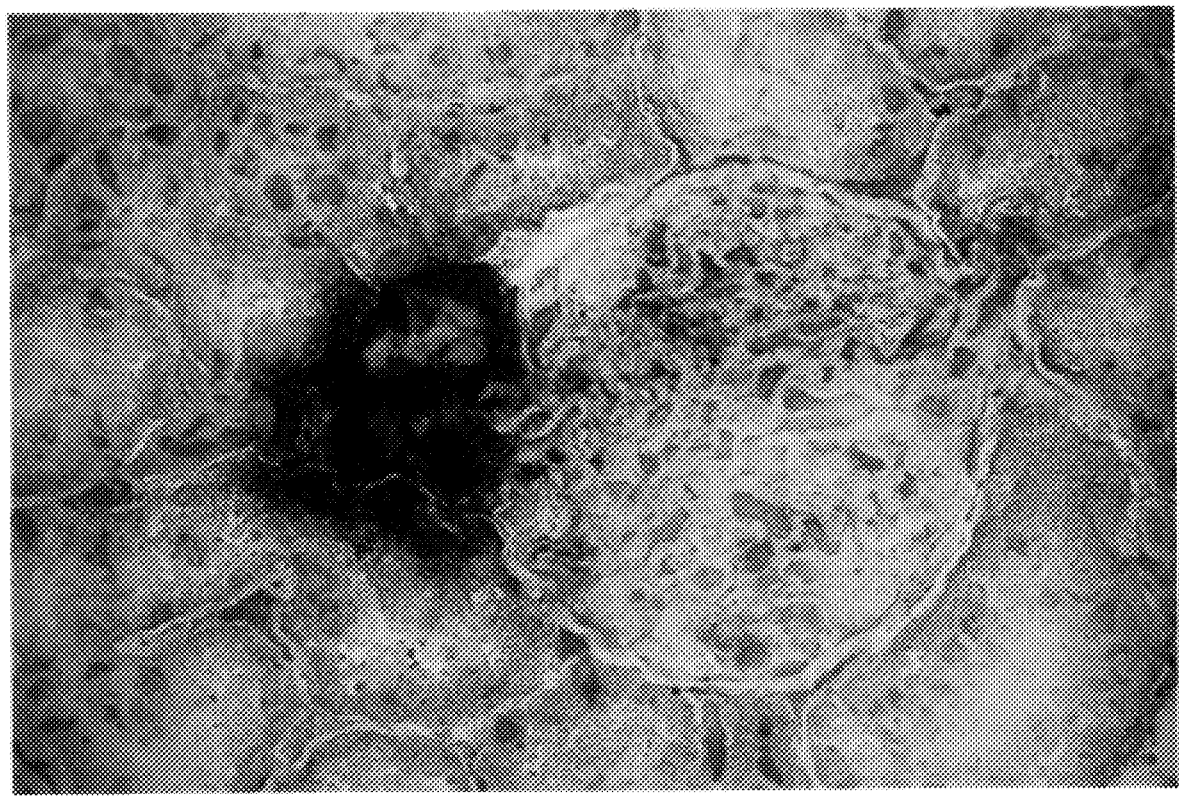
FIG. 7b is from a non-diabetic BB rat (×132).
Figure 7C:
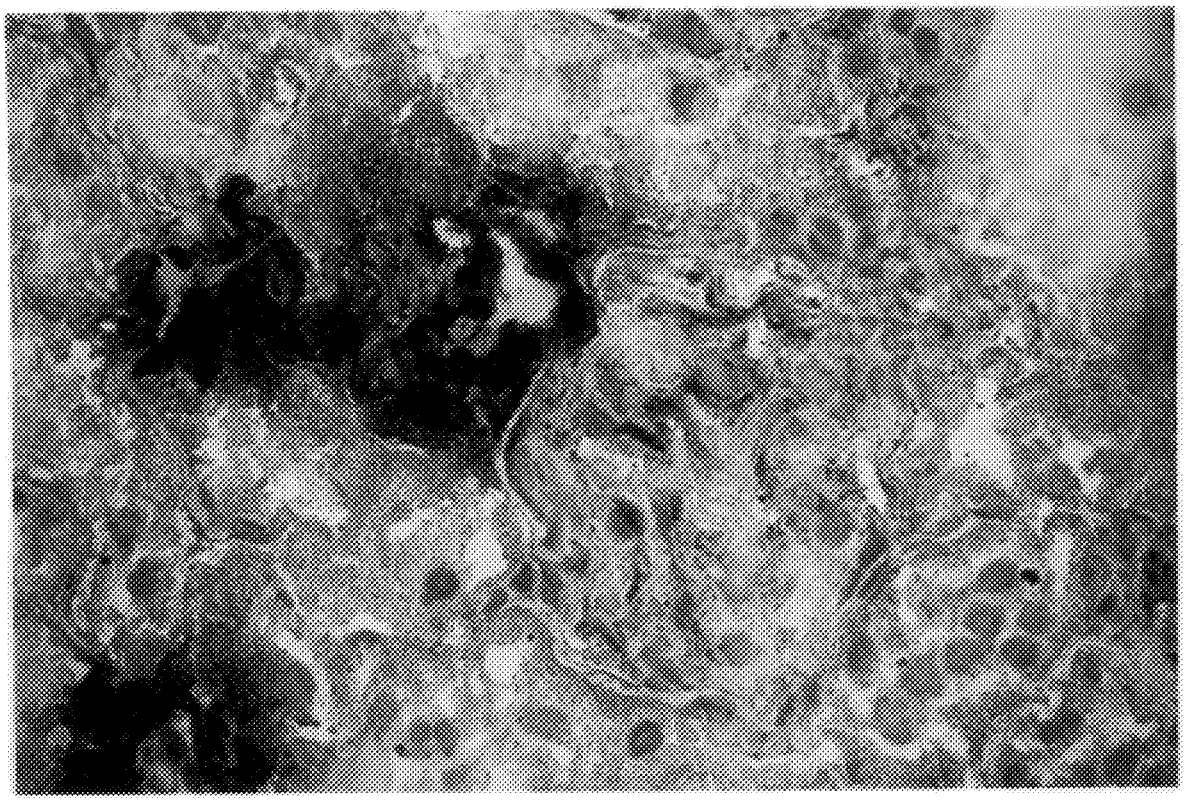
FIG. 7c is from a diabetic BB rat (×132); mesangial staining is indicated by arrow.
Figure 7D:
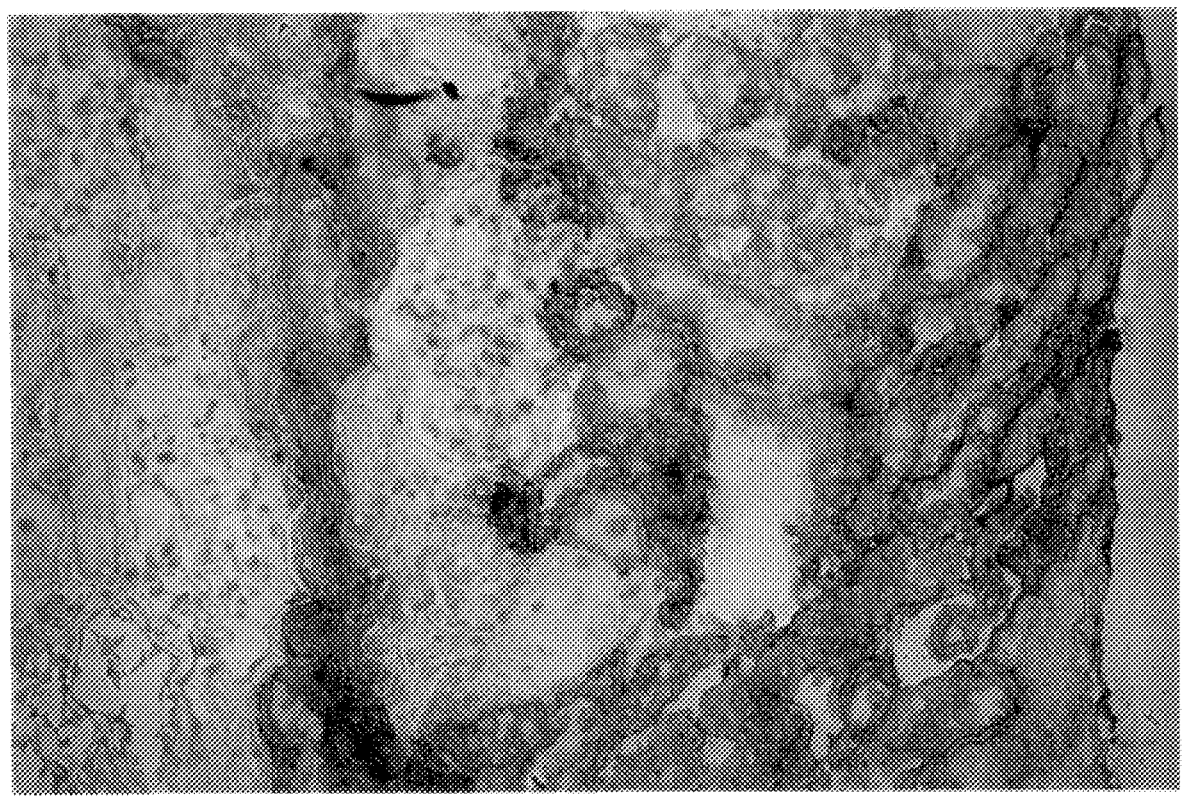
FIG. 7d is from a non-diabetic human (×50); glomeruli indicated by arrows.
Figure 7E:
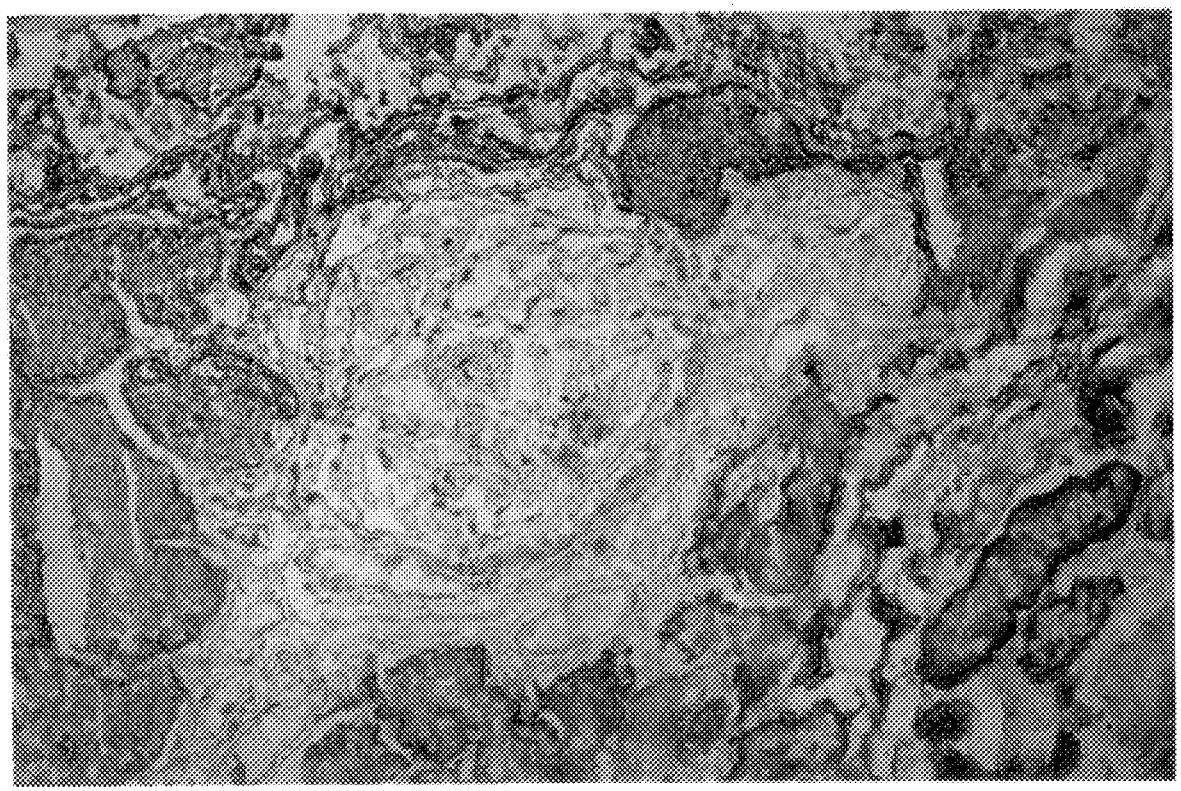
FIG. 7e is from a NIDDM human (×50).
Figure 7F:
FIG. 7f is from an IDDM human (×66); mesangial staining indicated by arrow.

In the diabetic BB rat kidneys (FIG. 4c) a distinct granular staining was located to the mesangial space as well as to the subendothelial area in the capillary loops, compared to the healthy BB rats (FIG. 4b). Otherwise there were no qualitative changes. Also in the diabetic rat kidneys, a very heavy staining of the juxtaglomerular arterioles, a few proximal tubules and many distal tubules was seen.

In the non-diabetic human kidney (FIG. 4d) granular deposits of Sulph I were not detected in the glomerulus but in juxtaglomerular arterioles and in a great number of tubular profiles; the tubular epithelial cells were strained but the basement membranes were negative. In the kidney of a NIDDM human patient (FIG. 4a) the glomeruli were unlabelled, as in FIG. 4d, but otherwise the staining was more heavy and distinct in a greater number of tubular profiles.

FIG. 4f shows the Sulph I labelling of a kidney section from a human IDDM patient. Compared to the non-diabetic human kidney, the glomeruli showed a granular staining in the mesangium and in some of the capillary loops. Furthermore, heavy staining was seen in the tubular profiles, more pronounced in the distal part.

Investigation of other tissues

As was expected, neural tissue was intensively stained by Sulph I. Rat lung, heart, liver, adrenal, spleen, lymph node, thymus tissue were not labelled by Sulph I.

Serological examinations

The result of the examination for sulfatide antibodies is seen from the following table. At diagnosis (first test) all the Type 1 diabetic patients displayed anti-sulfatide antibodies with a mean titre of 1:1131 (range 1:100–1:3200). At the second test six month later still 100% of the patients showed anti-sulfatide antibodies; the average titer was 1:728 (range 1:100–1:3200). Among the control persons only 11% displayed anti-sulfatide antibodies with a mean titer of 1:119 (range 1:100–1:400). Thus, the few antibody positive controls showed very low tires (weak positive) and if the cut off point for sulfatide antibody positive titres is set at the 1:400 titer, 0% of the controls were positive whereas among the diabetic patients 88% were positive at the diagnosis and 59% antibody-positive six month later. The antibodies were IgG, no IgM were detected.

|  |  | Neg | 1:100 | 1:400 | 1:800 | 1:1600 | 1:3200 |
|---|---|---|---|---|---|---|---|
| Patients, | n | 0 | 1 | 3 | 11 | 15 | 4 |
| diagnosis test | % | 0 | 3 | 9 | 32 | 44 | 12 |
| (n = 34) | acc. % | — | 100 | 97 | 88 | 56 | 12 |
| Patients, | n | 0 | 4 | 5 | 2 | 8 | 3 |
| second test | % | 0 | 18 | 23 | 9 | 36 | 14 |
| (n = 22) | acc. % | — | 100 | 82 | 59 | 50 | 14 |
| Controls | n | 119 | 14 | 2 | 0 | 0 | 0 |
| (n = 135) | % | 88 | 10 | 1 | 0 | 0 | 0 |
|  | acc. % | — | 11 | 1 | 0 | 0 | 0 |

50% of the patients showed antibodies against 3'-LM1 and 11% against GA1, both mainly in titers of 1:100.

I claim:

1. A method for treatment of prediabetes or diabetes in an individual by inducing in said individual a tolerance to a galactosylceramide-3-sulfate active agent of the formula

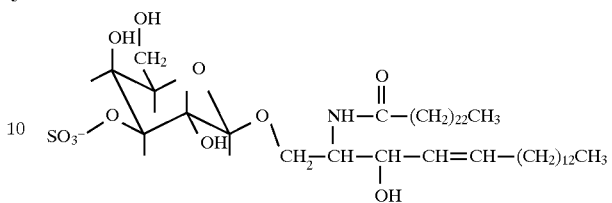

a lactosylceramide-3-sulfate active agent of the formula

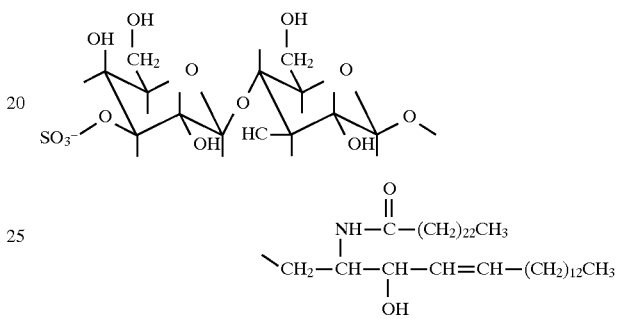

or a seminolipid active agent of the formula

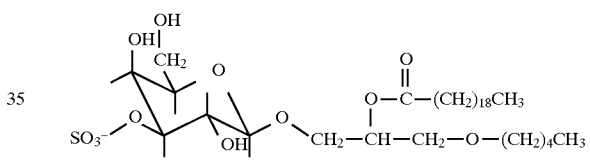

the method comprising administering the galactosylceramide-3-sulfate active agent, the lactosylceramide-3-sulfate active agent, or the seminolipid active agent to the individual.

2. A method of treating prediabetes or diabetes in an individual by raising in said individual suppressor or regulator cells or antibodies directed against lymphocytes recognizing a galactosylceramide-3-sulfate active agent of the formula

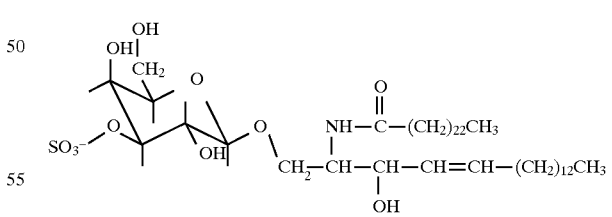

a lactosylceramide-3-sulfate active agent of the formula

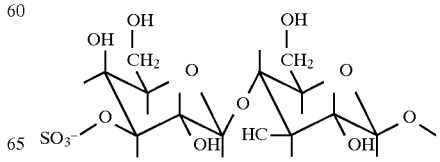

-continued

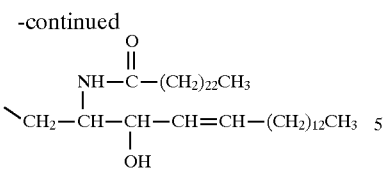

or a seminolipid active agent of the formula

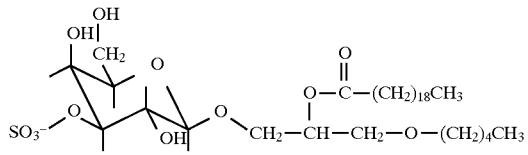

the method comprising administering lymphocytes having inhibited cytotoxicity and recognizing the galactosylceramide-3-sulfate active agent, the lactosylceramide-3-sulfate active agent or the seminolipid active agent.

3. A method for therapy of prediabetes or diabetes in an individual, comprising contacting the blood stream of the individual with an immobilized galactosylceramide-3-sulfate active agent of the formula

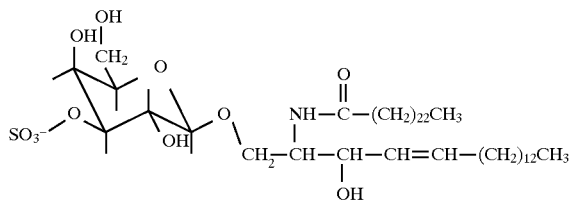

immobilized lactosylceramide-3-sulfate active agent of the formula

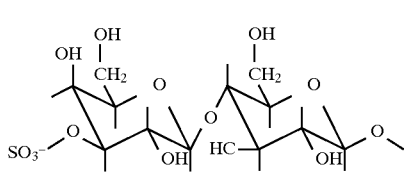

-continued

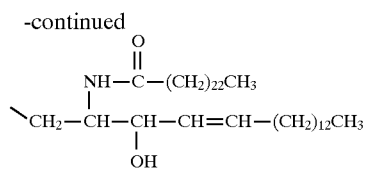

or immobilized seminolipid active agent of the formula

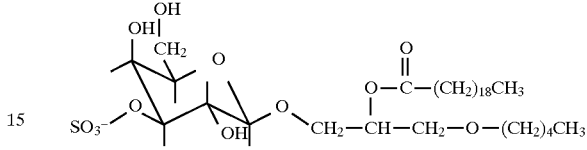

and removing from the blood stream of the individual antibodies or lymphocytes which recognize the galactosylceramide-3-sulfate active agent, the lactosylceramide-3-sulfate active agent, or the seminolipid active agent.

4. A method of detecting or quantifying islet cell antibodies in a sample, comprising contacting the sample with an antigen comprising a glycolipid having a galactose-3-O-sulfate moiety capable of binding to islet cell antibodies, and detecting or quantifying as islet cell antibodies those antibodies that bind to the glycolipid.

5. The method according to claim 4, wherein the glycolipid comprises a galactosylceramide-3-sulfate of the formula

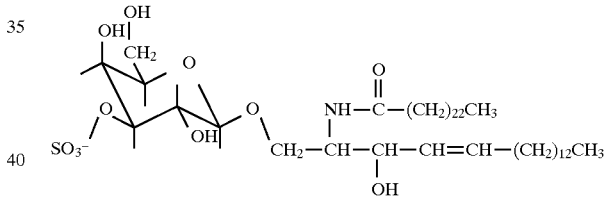

a lactosylceramide-3-sulfate of the formula

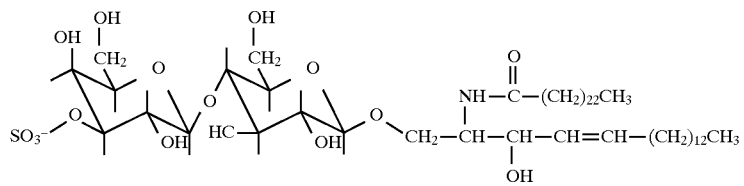

or a seminolipid of the formula

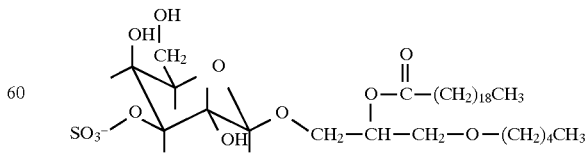

6. The method according to claim 4, wherein the glycolipid comprises a galactosylceramide-3-sulfate of the formula

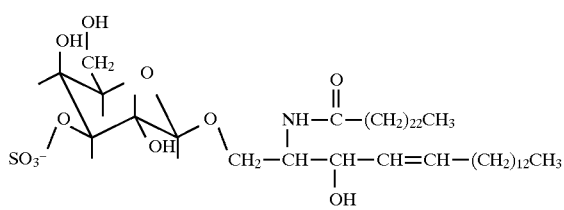

7. The method according to claim 4, wherein the glycolipid comprises a lactosylceramide-3-sulfate of the formula

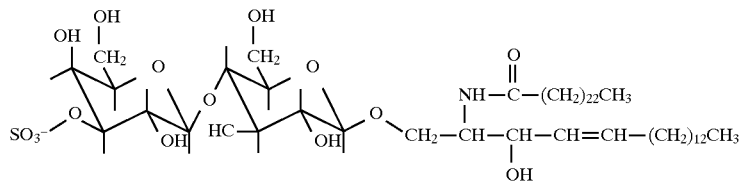

8. The method according to claim 4, wherein the glycolipid comprises a seminolipid of the formula

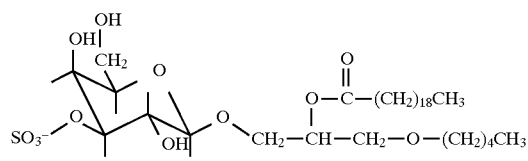

9. A method for detection of Langerhans islet cells, comprising histologically or cytologically staining a pancreatic preparation using an antibody or lectin directed against a sulfated glycolipid antigen comprising a galactosylceramide-3-sulfate of the formula

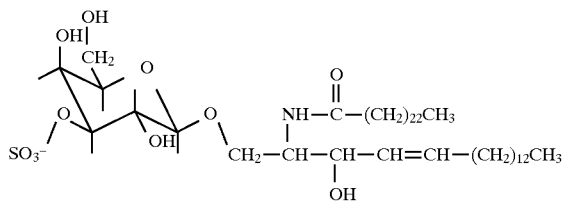

a lactosylceramide-3-sulfate of the formula

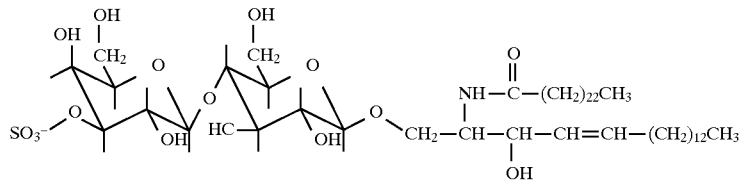

or a seminolipid of the formula

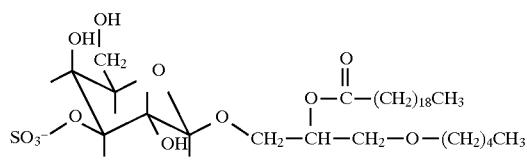

10. The method according to claim 9, wherein the antibody is Sulph I monoclonal antibody.

11. A method for treatment of prediabetes or diabetes in an individual, comprising administering to the individual a glycolipid therapeutic active agent having a galactose-3-O-sulfate moiety capable of binding to islet cell antibodies.

12. A method for treatment of prediabetes or diabetes in an individual, comprising administering to the individual a galactosylceramide-3-sulfate therapeutic active agent of the formula

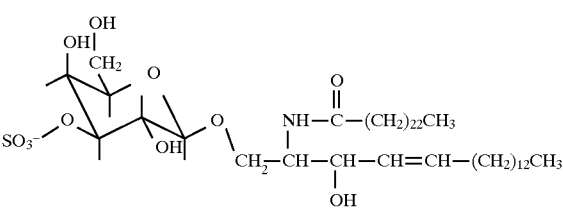

a lactosylceramide-3-sulfate therapeutic active agent of the formula

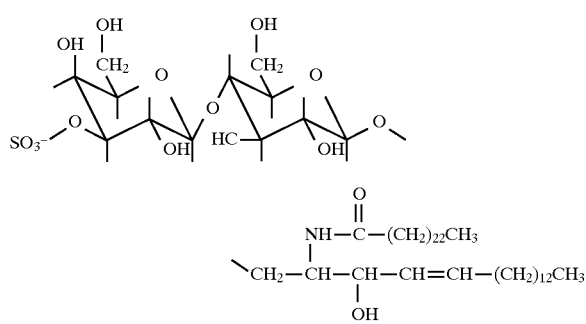

or a seminolipid therapeutic active agent of the formula

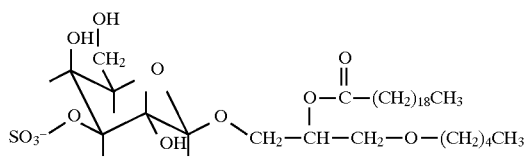

13. The method according to claim 12, wherein the galactosylceramide-3-sulfate therapeutic active agent of the formula

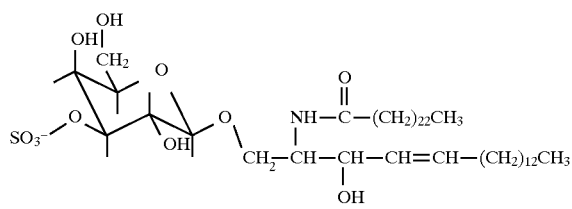

is administered.

14. A method for treatment of prediabetes or diabetes in an individual, comprising administering to the individual a lactosylceramide-3-sulfate of the formula

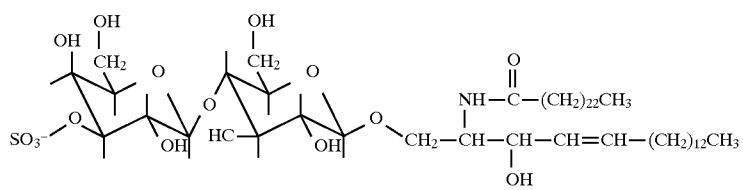

15. A method for treatment of prediabetes or diabetes in an individual, comprising administering to the individual a seminolipid of the formula

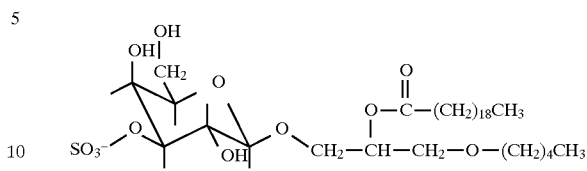

16. A method of detecting and optionally quantifying islet cell antibodies sin an individual, comprising contacting a sample of body fluid from the individual with an antigen comprising a glycolipid having a galactose-3-O-sulfate moiety capable of bonding to islet cell antibodies, and detecting and optionally quantifying as islet cell antibodies those antibodies that bind to the glycolipid.

17. The method according to claim 16, wherein the glycolipid comprises a galactosylceramide-3-sulfate of the formula

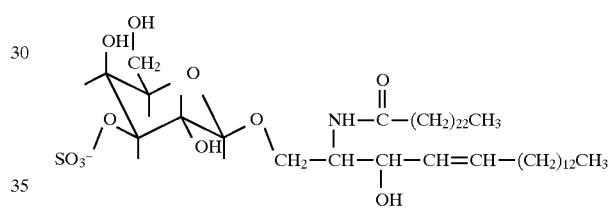

a lactosylceramide-3-sulfate of the formula

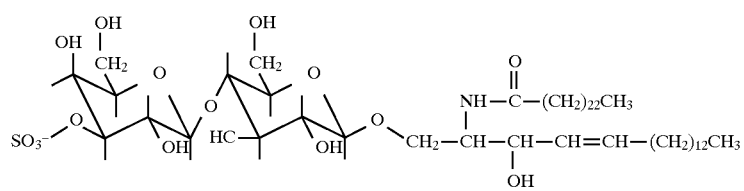

or a seminolipid of the formula

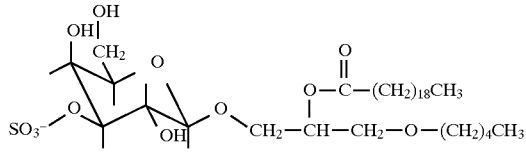

18. The method according to claim 16, wherein the glycolipid comprises a galactosylceramide-3-sulfate of the formula

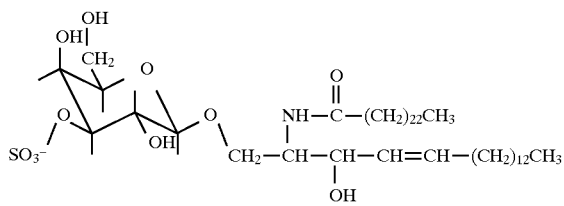

19. The method according to claim 16, wherein the glycolipid comprises a lactosylceramide-3-sulfate of the formula

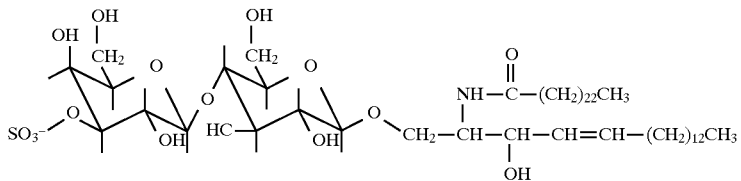

20. The method according to claim 16, wherein the glycolipid comprises a seminolipid of the formula

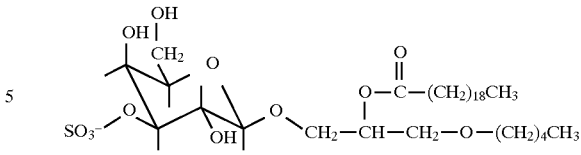

21. A method for monitoring development of prediabetes or diabetes in an individual, comprising contacting a sample of body fluid from the individual with an antigen comprising a glycolipid having a galactose-3-O-sulfate moiety capable of binding to islet cell antibodies, and detecting and optionally quantifying as islet cell antibodies those antibodies that bind to the glycolipid.

22. The method according to claim 21, wherein the glycolipid comprises a galactosylceramide-3-sulfate of the formula

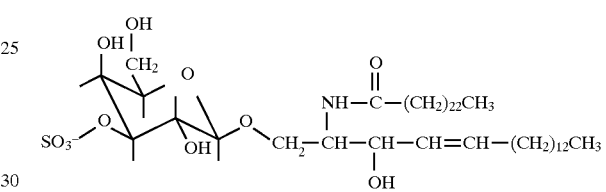

a lactosylceramide-3-sulfate of the formula

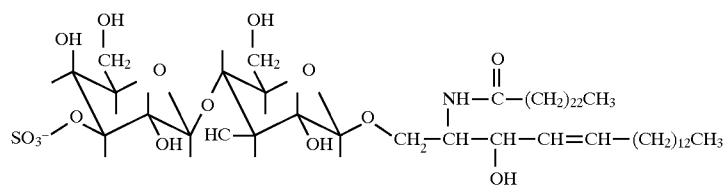

or a seminolipid of the formula

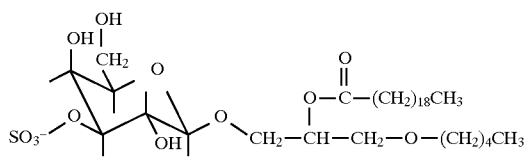

23. The method according to claim 21, wherein the glycolipid comprises a galactosylceramide-3-sulfate of the formula

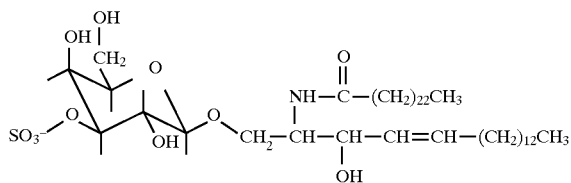

24. The method according to claim 21, wherein the glycolipid comprises a lactosylceramide-3-sulfate of the formula

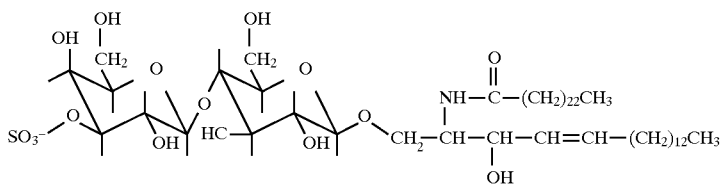

25. The method according to claim 21, wherein the glycolipid comprises a seminolipid of the formula

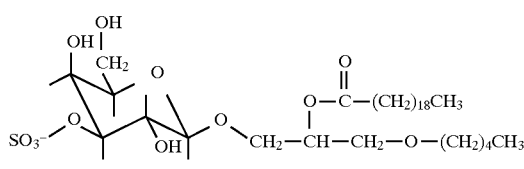

26. A method for prophylactic treatment against the development of prediabetes or diabetes in an individual being at risk of developing prediabetes or diabetes, comprising administering to the individual a therapeutically active agent comprising a glycolipid having galactose-3-O-sulfate moiety capable of binding to islet cell antibodies.

27. The method according to claim 26, wherein the glycolipid comprises a galactosylceramide-3-sulfate of the formula

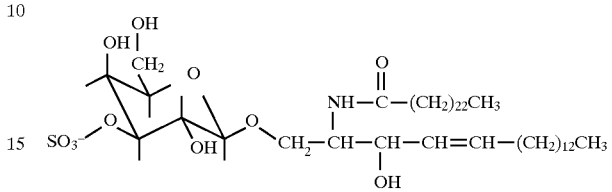

a lactosylceramide-3-sulfate of the formula

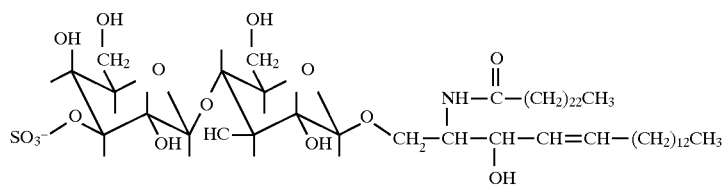

or a seminolipid of the formula

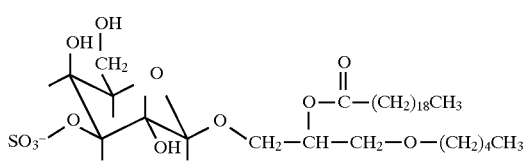

28. The method according to claim 26, wherein the glycolipid comprises a galactosylceramide-3-sulfate of the formula

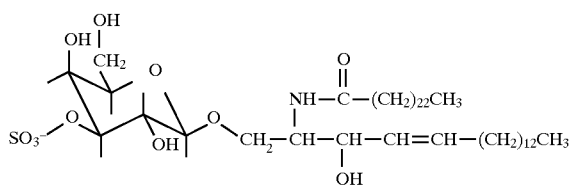
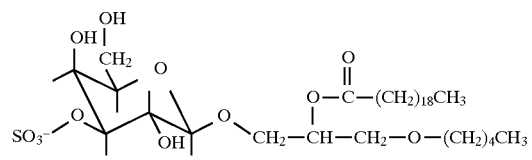
29. The method according to claim 26, wherein the glycolipid comprises a lactosylceramide-3-sulfate of the formula
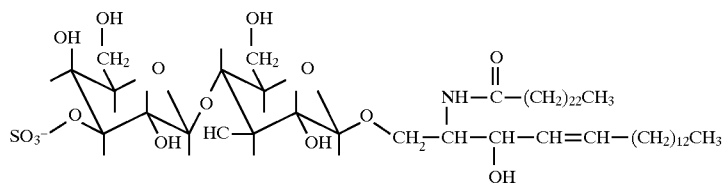
30. The method according to claim 26, wherein the glycolipid comprises a seminolipid of the formula
* * * * *

UNITED STATES PATENT AND TRADEMARK OFFICE
CERTIFICATE OF CORRECTION

PATENT NO. : 5,827,828
DATED : October 27, 1998
INVENTOR(S) : Karsten Buschard et al.

It is certified that error appears in the above-identified patent and that said Letters Patent is hereby corrected as shown below:

Claim 16, column 18, line 15, change "sin" to --in--.

Signed and Sealed this

Twenty-fifth Day of May, 1999

*Attest:*

*Attesting Officer*

Q. TODD DICKINSON

*Acting Commissioner of Patents and Trademarks*